US006440465B1

(12) United States Patent
Meisner (10) Patent No.: US 6,440,465 B1
(45) Date of Patent: Aug. 27, 2002

(54) TOPICAL COMPOSITION FOR THE TREATMENT OF PSORIASIS AND RELATED SKIN DISORDERS

(75) Inventor: Lorraine Faxon Meisner, Madison, WI (US)

(73) Assignee: Bioderm, Inc., Madison, WI (US)

( * ) Notice: Subject to any disclaimer, the term of this patent is extended or adjusted under 35 U.S.C. 154(b) by 0 days.

(21) Appl. No.: 09/562,400

(22) Filed: May 1, 2000

(51) Int. Cl.$^7$ .................. A61K 35/78; A61K 31/74; A01N 37/18
(52) U.S. Cl. .............. 424/725; 424/78.02; 424/766; 424/776; 514/2; 514/855
(58) Field of Search .................. 514/1, 2, 23, 25, 514/280, 855, 873; 424/725, 78.02, 766, 776

(56) References Cited

U.S. PATENT DOCUMENTS

| | | | |
|---|---|---|---|
| 3,122,535 A | * | 2/1964 | Krueger |
| 3,232,836 A | * | 2/1966 | Carlozzi et al. |
| 4,294,852 A | | 10/1981 | Wildnauer et al. |
| 4,647,453 A | | 3/1987 | Meisner |
| 4,722,936 A | | 2/1988 | Jacob |
| 4,772,591 A | | 9/1988 | Meisner |
| 4,818,521 A | | 4/1989 | Tamabuchi |
| 4,938,969 A | | 7/1990 | Schinitsky et al. |
| 4,983,382 A | | 1/1991 | Wilmott et al. |
| 5,140,043 A | | 8/1992 | Darr et al. |
| 5,310,742 A | * | 5/1994 | Elias |
| 5,401,773 A | * | 3/1995 | Noel |
| 5,639,740 A | * | 6/1997 | Crandall |
| 5,795,573 A | * | 8/1998 | Paradise |
| 6,011,067 A | * | 1/2000 | Hersh |
| 6,146,637 A | * | 11/2000 | Amari |

OTHER PUBLICATIONS

Mueller et al., Planta Med. (1994), 60(5): 421–4. The antipsoriatic *Mahonia aquifolium* and its active constituents; I. Pro–and antioxidant properties and inhibition of 5–lipoxygenase.*

Mueller et al., Planta Med. (1994); 60(5): 424–4. The antipsoriatic *Mahonia aquifolium* and its active constituents; I. Pro–and antioxidant properties and inhibition of 5–lipoxygenase.*

Sherry Lewin, "Vitamic C: Its Molecular Biology and Medical Potential," Academic Press, 1976, pp. 11, 14 and 41.

D. Darr, S. Combs, S. Dunston, T. Manning and S. Pinnell, "Topical Vitamin C Protects Porcine Skin from Ultraviolet Radiation–Induced Damage," British Journal of Dermatology, 1992, pp. 247–253.

Irwin Stone, "The Healing Factor Vitamin C Against Disease," Grosset & Dunlap, 1972, pp. 1, 39, 90–119.

G.G. Birch and K.J. Parker, "Vitamin C Recent Aspects of its Physiological and Technological Importance," John Wiley & Sons, 1974, pp. 136–145.

Monica L. Richey, M.D., Hobart K. Richey, M.D. and Neil A. Fenske, M.D. "Aging–Related Skin Changes: Development and Clinical Meaning, " Apr., pp. 49–64.

D. Cerimele, L. Celleno and F. Serri, "Physiological Changes in Ageing Skin," British Journal of Dermatology, 1990, pp. 13–20.

J. Graham Smith, Jr., M.D., Eugene A. Davidson, Ph.D., W. Mitchell–Sams, Jr., M.D., and Richard D. Clark, B.S., "Alterations in Human Dermal Connective Tissue with Age and Chronic Sun Damage," The Society for Investigative Dermatology, Jun. 27, 1962, pp. 347–350.

M. Tagawa, K. Uji and Y. Rabata, "The Application of Magnesium Ascorbate Phosphate to Skin Care Cosmetics," Paper No. 29, pp. 399–414.

Paul A. Seib and Bert M.Tolbert, "Ascorbic Acid: Chemistry, Metabolism and Uses," American Chemical Society, 1992, pp. 419–423.

Edward Staunton West, Ph.D., Wilbert R. Todd, Ph.D., Howard S. Mason, Ph.D. and John T. Van Bruggen, Ph.D., "Textbook of Biochemi," Fourth Edition, 1966, pp. 823–795.

* cited by examiner

Primary Examiner—Christopher R. Tate
Assistant Examiner—Michele C. Flood
(74) Attorney, Agent, or Firm—Sanford E. Warren, Jr.; Edwin S. Flores; Gardere Wynne Sewell LLP (57) ABSTRACT

Compositions and methods of use thereof for the treatment of psoriasis and related skin ailments are disclosed. The compositions include topical skin formulations of glucosamine in an emollient base such as moisturizing cream. In addition to glucosamine, the formulations may include keratolytic substances such as coal tar extract or salicylic acid. The formulations may also include glucosamine and antioxidant anti-inflammatory herbal extracts such as oleuropein and berberine in an emollient base.

21 Claims, 3 Drawing Sheets

| CLINICAL HISTORY OF SUBJECTS 1-4 | | | | |
|---|---|---|---|---|
| Age and sex | 1. 12 year old Female | 2. 77 year old Male | 3. 35 year old Male | 4. 49 year old Male |
| Racial/ehtnic background: | British, white | British, white | German, white | Chinese |
| Occupation: | Student | Real estate broker | Computer technician | Engineer |
| Affected areas: | Elbows, inner arm, scalp, left ear | Elbows, knees, wrists, scalp, and face. | Knees and shins | Arms, elbows, hands |
| Duration: | 6.5 years | 57 years | 4-5 years | 2 years |
| Severity | Elbows and arms severe. Ears and scalp moderate. | Severe thick scaly plaque psoriasis. | Moderate | Moderate |
| Previous therapy: | Betnovate, cortisone cream, other topicals | Synalar, Betnovate, X-rays, UV, oral cortisone, miscellaneous topical ointments | Sensitive to coal tar so used hydrocortisone creams and herbal ointments. All of above caused slow improvement during use, with flare ups after a few weeks. | Prescription creams. Creams worked after about 2 weeks but lesions soon recurred. |
| Response to formulation in Study 4 | Improvement noted in 2 days, lesions disappeared in 2 weeks with no redness or scarring | Elbows, hands and facial lesions disappeared after two weeks; the knees took four weeks. (His wife noted that this is the first time she has known him to be completely free of psoriasis.) | (Note: This subject was successfully treated with formulation in Study 3, and did not participate in Study 4. However, after treatment, his lesions disappeared in 4 days, with no recurrence in over 4 months) | Lesions improved in one week, disappeared in 2-3 weeks. |

Note: Subjects 1, 2 and 3 all have a family history of psoriasis.

*FIG. 1a*

| CLINICAL HISTORY OF SUBJECTS 5-8 | | | | |
|---|---|---|---|---|
| Age and sex | 5. 19 month old Male | 6. 80 year old Female | 7. 29 year old Female | 8. 4.5 year old Male |
| Racial/ehtnic background: | British, white | Italian, white | Portugese, white | American, black |
| Occupation: | N/A | Retiren librarian | Film/TV artist | Pre-school |
| Affected areas: | Face, legs, feet | Forearms, lower leg and shins, back of hands. 2 years | Elbows, face, knees, small patches on legs. 5years. | Elbows and knees |
| Duration: | 18 months | 2 years | 5 years | 2 years |
| Severity | Severe; exacerbated by allergens | Severe and very irritated | Moderate | Mild-Moderate |
| Previous therapy: | Aveenp, emu oil, hydrocortisone | Betamethasone, 1% cortisone, herbal creams | Cortisone cream, emu oil and steam baths. Cortisone did not work. Emu oil and steam baths helped. | Betnovate, various topical ointments. Temporary. Required repeated treatments. |
| Response to formulation in Study 4 | Improved in 3 days. Lesions gone in one week. Recurred on exposure to wheat, but formulation led to greatly accelerated healing compared to previous treatments. (See photo, Fig. 2a which was taken one day after twice daily application of formulation and bottom photo, Fig. 2b, which was taken one week later.) | Improved in 5-7 days. Lesions completely gone in 7-10 days. | Scabs and flaky skin were gone in 3 days. The redness was gone several days later. | Itching stopped after 2 days; lessions gone in one week (Note: He has an affected parent who also benefitted from this cream.) |

Note: Subjects 8 has a family history of ecczematous lesions.

TOPICAL COMPOSITION FOR THE TREATMENT OF PSORIASIS AND RELATED SKIN DISORDERS

TECHNICAL FIELD OF THE INVENTION

The present invention relates in general to the field of the treatment of psoriasis and related skin disorders, and more particularly to a non-toxic topical formulation that includes antioxidants and a pharmaceutically effective amount of an herbal extract for the treatment of psoriasis and related skin ailments.

BACKGROUND OF THE INVENTION

Without limiting the scope of the invention, its background is described in connection with disorders of the skin and, more particularly, to the general field of diseases that cause psoriasis, as an example.

Psoriasis is a common skin disease characterized by hyperplasia of keratinocytes resulting in thickening of the epidermis and the presence of red scaly plaques. The lesions in this chronic disease typically are subject to remissions and exacerbations. There are several patterns, of which plaque psoriasis is the most common. Guttate psoriasis, with raindrop shaped lesions scattered on the trunk and limbs, is the most frequent form in children, while pustular psoriasis is usually localized to the palms and soles. The classical inflammatory lesions vary from discrete erythematous papules and plaques covered with silvery scales, to scaly itching patches that bleed when the scales are removed. Despite a voluminous scientific literature and numerous treatment strategies, there is still no effective treatment for psoriasis that is completely without side effects.

The number of different and sometimes toxic treatments employed for amelioration of psoriasis is testimony to the resistant nature of this disease. Not only is moderate to severe psoriasis resistant to topical treatments, but because of its chronic and recurrent nature, systemic therapy or radiation is often required. The devastating nature of this disease is emphasized by the extent of the side effects that psoriasis sufferers are willing to endure to attain a remission to a disease that they know will recur sooner or later.

SUMMARY OF THE INVENTION

The present invention employs an emollient base such as moisturizing agents to promote skin re-epithelialization in order to diminish disfiguring lesions. The emollient base may include a large spectrum of suitable substances, including but not limited to creams, moisturizing creams, ointments, oils, waxes, gels, lotions, liquid suspensions or dispersions, emulsions, emulsions comprising oil in water, and the like, provided the emollient base is suitable for topical application on the skin, is substantially non-toxic and provides a suitable carrier for the non-emollient medicinal agents of the invention. A properly chosen emollient base may provide a certain amount of relief in itself for mild outbreaks of psoriasis or dermatitis.

The present invention also addresses the underlying T-cell disorder that results in an inflammatory condition. The present inventor has recognized that most, if not all, of the current therapies for psoriasis or similar T-cell mediated inflammatory skin conditions are designed to kill T-cells and to thereby ameliorate inflammation. It is possible that a major problem with the current treatments is that the therapy itself is so toxic that it may promote recurrence during healing. The toxicity of current treatments unleashes some or all of the cytokines that are associated with the promulgation of these chronic and often rebounding skin diseases.

It has been recognized by the present inventor that chronic inflammation leads to hyperproliferation and angiogenesis, and that agents that control inflammation also control angiogenesis and hyperproliferation. A prime example is corticosteroids, which are generally effective for treatment of psoriasis as well as atopic dermatitis. Corticosteroids' side effects however, include decreased connective tissue synthesis, weakened blood vessels due to the diminished connective tissue support, bone loss, increased infection, etc. In the present invention the agent selected is capable of topical administration to have a localized effect, completely non-toxic to normal skin, and an anti-inflammatory agent. Based on the inventor's previous experience with wound healing (Meisner, U.S. Pat. No. 4,772,591), D-glucosamine HCL was selected as one of the agents in the topical formulation for treatment of inflammatory skin diseases which, unlike the situation in wound healing, must work to oppose the activity of the T-cells. Although glucosamine has been shown to be effective in arthritis (Meisner, U.S. Pat. No. 4,647,453), inflammatory T-cells in the skin are different from those in arthritic joints. The T-cells of the skin express cutaneous lymphocyte antigen (CLA), whereas T-lymphocytes in the joint are CLA negative.

A topical skin preparation comprising glucosamine in an emollient base, therefore, is shown here to be an effective therapy for psoriasis and related skin ailments. As used herein, the term "skin" includes the scalp. The formulation of glucosamine in an emollient base should be suitable for topical application on human skin and may at least partially suppress, local to the area of topical application, the production of at least one cytokine that stimulates the proliferation of apoptosis-resistant keratinocytes.

Such a formulation suitable for topical application on mammalian skin may include glucosamine and extract from at least one herb that elicits at least one of the following biological effects: anti-inflammatory, antioxidant, antibacterial, antimicrobial, anti-pruritic, anti-platelet adhesion, vasodilation or keratolysis. For example, a formulation including approximately in the range of 5–25% glucosamine by weight; approximately in the range of 1–10% berberine by weight; approximately in the range of 0.5–7.5% oleuropein by weight; and approximately in the range of 47.5–93.5% emollient by weight, is shown to mitigate skin ailments local to the area of application.

The present invention also includes methods for the treatment of skin ailments. The methods include providing a formulation having approximately in the range of 5–25% glucosamine by weight; approximately in the range of 1–10% berberine by weight; approximately in the range of 0.5–7.5% oleuropein by weight; and approximately in the range of 47.5–93.5% emollient by weight; and topically applying the formulation to the affected skin. Another method includes providing a formulation having glucosamine and extract from at least one herb that elicits at least one of the following biological effects: anti-inflammatory, antioxidant, antibacterial, antimicrobial, antipruritic, anti-platelet adhesion, vasodilation or keratolysis; and topically applying the formulation to the affected skin. A further method for the treatment of skin ailments includes providing a formulation having glucosamine and at least one antioxidant anti-inflammatory in an emollient base and topically applying the formulation to the affected skin.

Although the mechanism of action of glucosamine is not well understood, it was shown almost 30 years ago that, in vitro, it significantly increases secretion of mucopolysaccharides by fibroblasts (N-acetylglucosamine and N-acetylgalactosamine also worked, but to a lesser degree) Karzel K. and Domenjoz R., "Effects of hexosamine derivatives and uronic acid derivatives on glycosaminoglycans metabolism of fibroblast cultures," *Pharmacology* 5: 337–345 (1971). This contrasts with the effects of steroids and non-steroidal anti-inflammatory drugs, which inhibit mucopolysaccharide metabolism by fibroblasts in vitro (and also appear to decrease connective tissue in vivo). Thus glucosamine, though anti-inflammatory, does not compromise normal connective tissue as do other anti-inflammatory agents. Glucosamine may work by inhibiting T-cell access to the skin as a result of the increased density of the connective tissue promoted by glucosamine. In contrast, following the use of the other agents the connective tissue tends to be compromised, leaving the skin more accessible and vulnerable to cellular infiltration. Therefore, the effect of glusosamine on T-cell induced inflammation may be explained as follows:

In normal skin aging there is a loss of connective tissue such that the dermis becomes thinner with age. Another effect of aging on the skin is the increasing incidence of skin cancer, particularly in photodamaged skin. Photodamaged skin is generally observed as having aged prematurely. Although it has been established that the main risk of non-melanoma skin cancer relates to sun exposure received before the age of 20, most skin cancers occur after age 70. This long latent period (as in other cancers with a long latent period that are associated with increasing atrophy, as occurs in the breast after menopause) may relate to the fact that although the requisite mutations for skin cancer may have been present for years (with the extent of exposure prior to age 20 the main determinant of skin cancer occurring much later in life), the mutated cells cannot expand into a region of dense connective tissue, nor can they compete with normal healthy cells in the absence of cumulative mutations. Moreover, the vascularity of aging tissues is compromised, which may partly explain the decreased immunocompetence of elderly skin. The skin of the elderly is much slower to react to antigens. The lethargic dermal immune response of the elderly suggests that the effector cells, which travel by the blood stream from the lymph nodes and must be extravasated at the site of injury, are thereby delayed.

T-cell transit in the young, on the other hand, is very efficient. Despite the dense connective tissue that must be traversed to the site of injury, T-cells in the young are able to do so quickly, perhaps due to a more accessible blood supply. Perhaps rapid transit accounts from the observation that atopic dermatitis and psoriasis occur so frequently in the young. That is, after conventional therapy following the initial insult, the connective tissue is compromised due to the corticosteroids or other therapy directed against activated T-cells, virtually inviting a recurrence of the complaint.

In contrast to the situation in the young, with increasing age, or with five or more years of immunosuppressive therapy as occurs in the case of organ transplantation (and possibly also after the toxic therapies used for psoriasis or atopic dermatitis), the density of the connective tissue is compromised. The skin is thinner and squamous cell cancer of the skin becomes more likely. It is of interest that PUVA treatments are only associated with a fourfold increase in basal cell carcinoma of the skin, no matter how many exposures have occurred, whereas the risk of SCC is dosage related. This observation with PUVA suggests that the thinning dermis (which is known to be due to UVA damage to collagen, rather than UVB) somehow promotes the development of SCC. The thinner dermis, as mentioned above, is also associated with depressed immunocompetence of the aging skin, as it rarely is seen in young skin except in the case of long-term immunosuppression. Therefore, the architecture of the skin plays a major role in immune modulation and glucosamine may play a major role in maintaining the normal architecture. Nonetheless, since psoriasis and atopic dermatitis may strike at a young age, psoriasis is clearly not related to only the thinning skin, in contrast to skin cancer and decreased skin immune response. It is postulated herein that the denser skin, with increased mucopolysaccharides promoted by glucosamine, attenuates the cytokines elaborated by the activated T-cells. Attenuation of the T-cell cytokines inhibits the inflammatory effect of the cytokines, possibly through dilution. Even in dense young skin, this may be the effect of the glucosamine: to bind nonspecifically to cytokines or to entrap the cytokines in a muccopolysaccharide "net", thereby inhibiting the inflammatory effect of the cytokines on the skin.

It has been suggested that oral glucosamine might be effective in treating psoriasis but our experiments demonstrate that topical application of glucosamine is preferred for a primary effect on the skin. The effect of glucosamine on arthritis suggests that it may be a systemic anti-inflammatory agent, but systemic anti-inflammation may not be desirable or preferred for the treatment of psoriasis and related skin ailments.

Together with agents that are observed to inhibit T-cells, or are keratolytic such as coal tar extract or salicylates such as salicylic acid, or, as demonstrated herein, with herbs having antiinflammatory, anti-bacterial, vasodilatory and/or anti-pruritic effects, a surprising synergistic response is elicited over glucosamine alone. A number of appropriate herbs that may work synergestically with glucosamine, for the present invention, are known to those of skill in the art in light of the present disclosure. Two herbs were selected that appear to work synergistically to actually cure resistant psoriatic lesions as well as resistant atopic dermatitis which has proved completely resistant to a number of standard therapies. The two herbs selected to demonstrate the required interaction are:

(1) Oleuropein: Olive leaf extract. This is a glucoside to which a great many properties have been attributed in the herbal literature. It may work in the present formulation by helping to restore the normal health of the skin by aiding in repair. Oleuropein has been called a natural antibiotic because it has been claimed to relieve symptoms of all types of infections: fungal, bacterial, viral, and parasitic. Any agent to which so many different mechanisms are attributed is generally suspect, but it has been suggested that there is an anti-viral constituent in oleuropein, calcium enolate, which is obtained after mild acid hydrolysis, and is said to work by inactivating viruses by dissolving their outer envelope. Aside from claims in the health food industry, it has long been known in Greece that during the olive harvest, the skin problems of those climbing the trees improved considerably. As a result, products containing olive leaf extract have been used in Greece for decades for treatment of psoriasis. Its efficacy in treating psoriasis, however, is generally based on hearsay, and is not documented in any medical studies. All that can be claimed with certainty is that the olive leaf extract is rich in natural antioxidants which are theoretically capable of attenuating the effects of the free radicals generated as the result of the $CD8^+$ related cytokines. Because of the traditional use of the olive leaf extract, and its concentration of antioxidants, this chemical was selected to be used here in a formulation for treating psoriasis of the skin. Although any chemical to which so many varied curative powers are attributed is unlikely to have any specific effect, based on its composition, which should reduce inflammation to some extent due to the antioxidants, the olive leaf extract was selected as one of the constituents of the present formulation.

(2) Berberine: Oregon grapeseed extract. This herb is also said to possess antimicrobial activity, as well as being antifibrotic, anti-platelet adhesion and a natural protectant against heart disease and circulatory complaints. It has been widely used for the treatment of inflammation in Chinese herbal medicines, and has also been used to treat diarrhea in dysentary, as well as to treat non-insulin dependent diabetes mellitus. Without going exhaustively into the list of conditions for which berberine has shown a possible effect, which includes those listed above as well as for chloroquin resistant malaria and for treating ventricular tachyarrhythmias by improving left ventricular function with the production of mild systemic vasodilation. It is clear that this compound has a long track record for safety, may be anti-inflammatory, and may cause mild vasodilation that would enhance absorption of a topical preparation, and this is why Oregon grapeseed extract was included in the present formulation.

The synergistic effects of the two herbs and glucosamine results in a non-toxic highly effective treatment for psoriasis that is without the side effects observed with virtually all other therapies for moderate to severe psoriasis (mild psoriasis may be successfully treated with proper moisturizing). As illustrated by the following studies, the most common over-the-counter treatment for psoriasis, namely coal tar, may be made more effective by the use of glucosamine, even at low concentrations of coal tar. The herbal combination with glucosamine may be used to treat severe cases which berberine alone cannot.

BRIEF DESCRIPTION OF THE DRAWINGS

For a more complete understanding of the features and advantages of the present invention, reference is now made to the detailed description of the invention along with the accompanying figures in which corresponding numerals in different figures refer to corresponding parts, if applicable, and in which:

FIG. 1a is a table describing the clinical history of subjects 1–4 of one embodiment of the present invention;

FIG. 1b is a table describing the clinical history of subjects 5–8 of one embodiment of the present invention;

DETAILED DESCRIPTION OF THE INVENTION

Psoriasis lesions may be disfiguring and often result in psychological problems. Numerous psoriasis support groups exist to help suffers cope with the disease. It is generally a lifelong disease with exacerbations and remissions, with a mean age of onset of 27.8 years. Two percent of cases occur in infants. Psoriasis is estimated to affect two percent of the U.S. population, and its worldwide prevalence is 0.1 to 3 percent. There is a significant genetic component, since 35 percent of patients have at least one affected relative. The lifetime risk without affected relatives is 4 percent, but it is 28 percent if one parent is affected, and 65 percent if both parents are affected. The genetic etiology is supported by its association with a specific genotype HLA-Cw6. Other chronic eczematous skin conditions include atopic dermatitis, which also has a genetic component, though it is less well defined than for psoriasis. Atopic dermatitis is also characterized by disfiguring red scaley lesions, inflammation, and resistance to therapies that are almost the same as those used to treat psoriasis.

Psoriasis is caused by unknown factors that stimulate T-lymphocyte activation, proliferation, and cytokine release that leads to hyperproliferation of keratinocytes that overproduce Bc1-x (instead of normal Bc1-2) and therefore resist apoptosis. The association with Bc1-2 is not unexpected in view of the strong association with HLA-Cw6, and the fact that the predominant T-cell in psoriatic lesions is $CD8^+$.

Cells that mediate the skin manifestations of psoriasis reside primarily in the epidermis or at the dermal-epidermal interphase. Although a few $CD4^+$ T-cells may be present in lesional skin, the majority of the cells are $CD8^+$ lymphocytes that secrete the cytokines interleukin-2 and interferon-gamma. These cytokines drive proliferation of keratinocytes and endothelial cells of the microvessels in affected skin. The keratinocytes in psoriatic lesions neither differentiate normally into compact and protective stratum corneum, nor are these cells subject to apoptosis like normal keratinocytes. This is because the psoriatic keratinocytes, due to the effect of IFN-gamma, contain Bc1-x, which protects against Fas-mediated apoptotic proteins. Normal cells that contain Bc1-2 are susceptible to Fas-mediated apoptosis.

Although psoriasis manifests as a skin disorder, it is believed to be a disease of impaired or defective cell-mediated immunity. Dysregulated lymphocytes produce cytokines that stimulate the proliferation of apoptosis-resistant keratinocytess. The same resistance to therapy also characterizes atopic dermatitis, another skin condition associated with T-cell activation with elaboration of cytokines that lead to epidermal hyperplasia. Atopic dermatitis is believed to result from an exaggerated cutaneous immune response to antigens, but the main T-cells activated are the $CD4^+$ cells that secrete type-2 cytokines such as interleukin-5, which leads to expansion of eosinophils, and IL-10 that leads to a reduction in cell mediated immunity resulting in increased infections of the skin.

Topical treatments have been used as an adjunct to other therapies in patients with moderate to severe psoriasis, although such treatments may suffice alone for those with limited to moderate psoriasis. Topical therapies, include coal tar preparation (1–5% by weight). Although this is the most frequently used topical therapy, coal tar has a bad odor and stains clothing. Coal tar is thought to be effective for psoriasis because it is toxic to T cells, but is not toxic to skin cells.

Another mainstay of topical therapy includes topical steroids, but long term use of fluorinated corticostetoids (which are more effective than hydrocortisone) may lead to striae, telangiectasis and ecchythmosis. Topical anthralin cream (1%) or high dose/short duration anthralin in 1% salicylic acid in petroleum may be effective, or the topical synthetic retinoid tazarotene, may also provide short-term relief, although these are often irritating. Other treatments involving retinoids are described, for example, in U.S. Pat. Nos. 3,934,028; 3,966,967; 4,021,573 and 4,216,224. Other topical agents such as calcipotriene, a vitamin D analogue (vitamin D3 or calcipotriol) may also provide temporary relief, while keratolytics such as salicylic acid can help in removing the thick scales from the psoriatic plaques. See, for example, U.S. Pat. No. 4,483,845 "Systemic Treatment of Psoriasis Using Certain Salicylates." Coal tar extract, the most common topical treatment, is generally considered to be a mild skin irritant, a weak antiseptic and a keratolytic agent. Nevertheless, coal tar extract and salicylates are generally considered substantially non-toxic in spite of a certain amount of skin irritation associated with their use. Despite their limited effectiveness and the discomfort associated with their use, these topical therapies are the mainstay of treatment for moderate psoriasis while they are used as adjunctive therapy in patients with more severe disease.

It is commonly observed that natural sunlight may be beneficial for treatment of psoriasis, and this has led to the use of UV radiation therapy. Examples are shown in U.S. Pat. No. 4,153,572 "Ultraviolet Emitting CeYMg Aluminate Lamp Phosphor for Psoriasis Treatment" and U.S. Pat. No. 4,558,700 "UV Radiation Device for Phototherapy of Dermatoses, Especially Psoriasis." UVB radiation (280–320 nm) of affected areas is one of the most common treatments for moderately severe psoriasis, with its efficacy enhanced by coating the skin with a tar containing emollient prior to the radiation. In normal skin, UVB increases production of transforming growth factor alpha (TGF alpha) by keratinocytes, which accelerates their rate of proliferation and increases epidermal thickness. UVB also increases leukocytic infiltration in normal skin, and activates neutrophil effector functions, which is why excess sun exposure damages normal skin. In psoriatic skin, however, UVB reverses hyperplasia, decreases proliferation, and restores the skin to normal by depleting the T lymphocytes from the psoriatic epidermis.

UVB exposure is not toxic to psoriatic keratinocytes at doses which kill epidermal T cells, although there is little effect on dermal lymphocytes due to the minimal penetration of UVB into the dermis (Krueger, J. G., et al., "Successful Ultraviolet B Treatment of Psoriasis is Accompanied by a Reversal of Keratinocyte Pathology and by Selective Depletion of Intradermal T-cells," *J. Exp. Med.* 182: 2057–2068, 1999). This is why the most common therapy involves UVA radiation, with longer wave length (320–380 nm) enabling the radiation to extend into the dermal layer. One common form of treatment requires that the patients ingest psoralen orally, and receive UVA radiation about an hour later, which is why this treatment is called PUVA. PUVA therapy is effective for patients with severe psoriasis and must be repeated two or three times weekly for eight weeks. *Mayo Clinic: Update on the Treatment of Psoriasis*, Mayo Clinic Update 14(3):7–8, 1998. PUVA is known to be immunosuppresive though the short-term side effects are related to those associated with oral psoralens, and include nausea, vomiting, and headache. Id. PUVA treatment generally leads to a temporary remission. Hence, patients typically receive many treatments over their lifetime. PUVA intentionally inflicts genotoxic damage to the skin in the course of killing the T-lymphocytes in the dermis and epidermal-dermal interface. It is, therefore, not unexpected that patients who receive more than 250 such treatments have a 5.5 fold increase in their risk of malignant melanoma (Peritz, A. E., et al., "Psoriasis, PUVA and Skin Cancer—Molecular Epidemiology: The Curious Question of T→A Transversions," *J. Invest. Dermatol.*, Symposium Proceedings 4: 11–16, 1999), while those receiving, over 337 PUVA treatments have a 68 fold increased risk of squamous cell carcinoma (SSC). The risk is 26 fold increased for 160 to 336 PUVA treatments. Even for those with low exposure (under 100 treatments) the risk of SCC is five times background. Given the excessive exposure received by psoriatic skin, one would expect even higher risks of SCC in psoriatic plaques. The relatively infrequent malignant transformation of psoriatic lesions into SCC, however, is proof that psoriasis is not just a hyperplastic disorder. Because the keratinocytes are so resistant to apoptosis, they are more resistant to malignant transformation, as has been observed in senescent cells. Indeed, the Bc1-x expression in psoriatic keratinocytes may not be so much due to the elaboration of IFN-gamma by the $CD8^+$ cells as due to the fact that the hyperproliferation and treatment-induced sloughing of keratinocytes have resulted in accelerated senescence in the affected cells. The normal skin adjacent to psoriatic plaques is also exposed in the course of PUVA therapy and it is likely that these cells give rise to the skin cancers that are often observed after 15 years of therapy.

Other systemic therapy includes X-ray to the affected regions, as well as oral cortisosteroids, because of its immunosuppressive effect on the cytotoxic T lymphocytes. Another frequently used chemotherapeutic agent is methotrexate, which is particularly beneficial in patients with psoriasis, although its disadvantages include leukopenia and cumulative hepatic toxicity that requires frequent monitoring by fine needle biopsies of the liver. Cyclosporine has recently been approved for treatment of severe psoriasis, although long term therapy with this drug may result in hypertension and potential nephrotoxicity (see Mayo Clinic citation, above). Hydroxyurea, another cancer chemotherapeutic agent, is moderately effective in controlling psoriasis, but its use is also limited by hematologic side effects. Acitretin, a synthetic retinoid, may also be beneficial although retinoids are teratogenic, and patients using acitretin may experience extreme dryness of mucous membranes and an increase in arthalgias, as well as increased blood triglycerides and, less commonly, increased blood levels of cholesterol and hepatic enzymes may occur.

There are other agents that have been used for control of psoriasis, but they have even more side effects and lower effectiveness than the therapies described above. Treatment of moderate to severe psoriasis may be very devastating, yet patients are willingly undergoing such therapies in order to ameliorate their disease. In addition to the therapies discussed above, the following United States Patents are examples of other modalities that have been developed for psoriasis, to illustrate the extreme measures some people will take to treat the disease:

U.S. Pat. No. 4,788,057 "Process for the Treatment of Psoriasis using Typhoid Vaccine"

U.S. Pat. No. 4,853,388 "Method for Treating Psoriasis with Cytotoxic Agents"

U.S. Pat. No. 5,501,705 "Method for the treatment of Psoriasis with Electric Current"

U.S. Pat. No. 5,527,350 "Pulsed Infrared Laser Treatment of Psoriasis"

U.S. Pat. No. 5,760,006 "Anticonvulsant Derivatives useful in Treating Psoriasis"

U.S. Pat. No. 5,800,831 "Psoriasis Treatment with Polymer Film"

U.S. Pat. No. 5,833,996 "Treatment of Psoriasis using Dead Cells of Mycobacterium Vaccae"

U.S. Pat. No. 5,836,999 "Method and Apparatus for Treating Psoriasis using Pulsed Electromagnetic Radiation"

U.S. Pat. No. 5,976,505 "Method for Cryogenically Treating Psoriasis with Liquid Nitrogen or Liquid Nitrous Oxide"

It is because of the often harsh treatment strategies that dominate psoriasis therapy that the following formulations were designed, the objective of which is to preserve the skin surfaces without subjecting the cells to hyperproliferation, without compromising the immune system, and without causing changes that result in an increased risk of skin cancer or other conditions.

Similarly, effective therapeutic agents are also limited for treatment of atopic dermatitis, and even effective therapies often have a very short-term effect. Most treatments are toxic or may have long term consequences, as is the case for psoriasis. Steroids are currently the most widely used topical treatment, but since these are often ineffective in controlling inflammation, UVA or UVB therapy is also used; as is coal tar. Immunosuppressive therapy using cyclosporine, topical tacrolimus (used in organ transplantation); methotrexate (though it is not as effective as it is in psoriasis), and other similar chemotherapeutic agents are also used because of their effects on T-cell mediated immune responses, as are azathioprene and interferon gamma. Yet, although these aggressive therapies may produce remissions, the remissions tend to be brief and often soon require additional therapy, subjecting the patient to the choice between toxic therapies and a devastating skin disease.

Studies were conducted on human subjects suffering from varying degrees of psoriasis to test different formulations of glucosamine with suitable synergistic components for effectiveness in ameliorating the skin condition of the subjects.

The subjects who participated in the following studies are described in greater detail in FIGS. 1a and 1b. Reference is made to FIGS. 1a and 1b in the description of the following studies.

Study 1: This study involved subjects 1, 2, and 3 (FIG. 1a). The following preparation was used once or twice daily:
moisturizing cream: 77.4% by weight
coal tar extract: 3% by weight
D-glucosamine HCL: 20% by weight
Results Subject 1 noted some improvement after two weeks, but the lesions were still present, and the skin retained its redness. Subject 2 found that it stopped itching on his legs after a few days, but then no further effect was noted, and the itching returned. Subject 3 turned out to exhibit some sensitivity to coal tar and after two applications had to discontinue use due to the resulting increase in inflammation. Apparently this subject had been aware of this sensitivity, but had agreed to test the formulation without knowledge of its constituents, which had been described as those commonly available without a prescription from pharmacies or health food stores.

Conclusion

None of the subjects had benefitted from the over-the-counter concentration of 3% coal tar in the past, but subjects 1 and 2, for the first time, experienced initial relief, which may be partly due to the anti-inflammatory effect of the glucosamine coupled with the suppressive effect of the coal tar on activated T-lymphocytes. The fact that subject 3 was unable to use any medication containing coal tar emphasized that some individuals with psoriasis may have extreme sensitivity to this commonly used agent. An alternative keratolytic, such as salicylic acid in the range of approximately 1–5% by weight, or other suitable salicylates, may be an effective substitute for subjects sensitive to coal tar.

Study 2: This experiment involved subjects 1 and 2 only, plus several others with mild psoriasis.

Formulation:
Moisturizing cream base: 92% by weight
berberine (Oregon grapeseed extract): 5% by weight
oleurolein (olive leaf extract): 3% by weight
Results This formulation had no effect on subject 1, whereas subject 2 noted a slight decrease in inflammation, but the psoriatic lesions were still present. This formulation had been previously tested on a number of subjects with mild to moderate psoriasis who found it to be helpful. However, based on the present test with subjects having moderate to severe psoriasis, there was little effect.

Conclusion

As previously stated, a good moisturizing agent may be adequate for mild psoriasis. Since this formulation contained a relatively high berberine concentration, it is apparent that the formulation of berberine augmented by oleuropein is not adequate for more severe disease.

Study 3: This study involved subjects 1, 2, and 3.

Formulation:
moisturizing cream: 82.5% by weight
berberine: 4.7% by weight
oleuropein: 2.8% by weight
D-glucosamine HCl: 10% by weight
Results Subject 1 noted some improvement, but after two weeks of use, the affected areas were still red and somewhat inflamed. Subject 2 noted a little improvement, but less than he had experienced with the first two formulations. Subject 3 improved after 4 applications, but it should be noted that his lesions were less severe than the other subjects in the study, despite a family history of very severe psoriasis (his father and uncle).

Study 4: This study involved subjects 1, 2, 4, 5, 6, 7 and 8. FIGS. 1a and 1b.

Formulation:
moisturizing cream: 76.5% by weight
berberine: 3.5% weight
oleuropein: 2% by weight
glucosamine: 18% by weight
Results Subject 1 noted improvement in two days; and the lesions had completely disappeared after two weeks.

Subject 2 had a similar response, with the lesions disappearing from all sites, except for a slight residual on his knees. Although all of his lesions had completely cleared by two weeks except for his knees and shins, the latter cleared after an additional two weeks of use. It was noted by his wife that this was the first time she had ever seen him without psoriasis despite the many therapies he had been subjected to in the past which included X-radiation, UVA and UVB, oral steroids and topical steroids, and other modalities. These therapies had most likely compromised the underlying tissues, making his improvement all the more spectacular after a disease that had resisted all therapy for 57 years. Although he had partial remissions in the past with the above treatments his lesions never completely disappeared until he used the present formulation.

Subject 4, who is of Chinese descent, suffered with psoriasis for two years and had been treated with various creams prescribed by a dermatologist for the lesions on his arms, elbows, and hands. Although the previous treatments had been effective, the psoriatic lesions would return after two weeks or so, and thus far two months have passed without a recurrence since using the formulation in study 4, which has not only produced a longer remission, but demonstrated efficacy that was very noticeable in just one week, with complete disappearance of the lesions within two to three weeks.

Figure 2A:
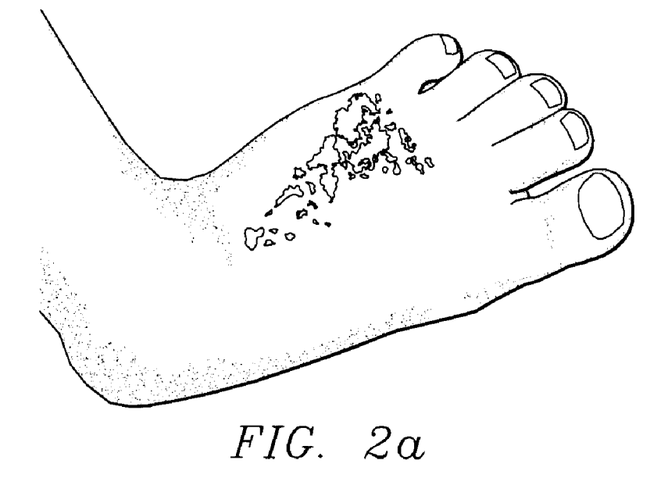
FIG. 2a is a photograph showing a foot of subject 5 one day after treatment with one embodiment of the present invention.
Figure 2B:
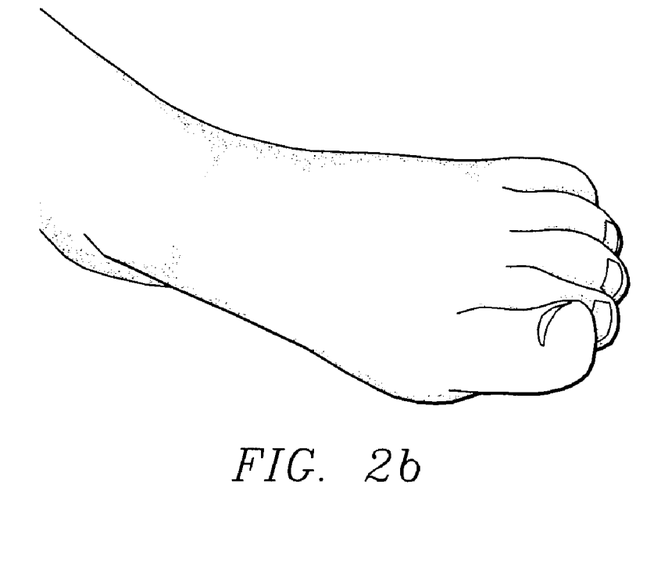
FIG. 2b is a photograph showing the foot of FIG. 2a one week after treatment with one embodiment of the present invention.

Subject 5 is a 19 month old toddler of Caucasian ancestry who has had red oozing and itching lesions on his feet and lower legs since infancy. This appears to have had an allergic component, as is often the case with eczematous lesions presenting in infancy. When the experimental treatment was first applied, because of the presence of open lesions, the subject found it very irritating and tried to rub it off and to remove the socks which were put on his feet to prevent removing the preparation. By the morning after the first application the lesions had crusted over, as shown in FIG. 2a. Although he was very suspicious, the subject allowed the treatment to be applied that next evening. Within a week the lesions had completely disappeared, as shown in. FIG. 2b. When he was subsequently exposed to wheat, however, the lesions returned but remitted within two days after using the formulation. Despite using a number of therapies, including topical hydrocortisone, the subject had never experienced complete relief before, and now, when after exposure to an allergen (he has many allergies in addition to gluten), he feels his feet beginning to itch, the subject runs to the refrigerator and points to the cream, and is now very eager to have it applied as it brings him almost instant relief. Therefore, although the formulation of Study 4 does not cure the cause of the the subject's skin eruptions, which has an allergic etiology, it very quickly eliminated the resulting lesions.

Subject 6 is an 81 year old woman of Italian descent. After suffering with psoriasis that had gotten increasingly severe over the past 10 years, necessitating many visits to the dermatologist, nothing gave her lasting relief until she used formulation 4, described above.

Subject 7 is a 29 year old woman with psoriasis on elbows, face, knees, and small patches on her legs. In the past, the subject generally experienced temporary relief with cortisone creams after several weeks of use, but when using the present formulation, her lesions were completely gone within 3 days, although the redness persisted for a few more days.

Subject 8 is a four and a half year old black male with lesions on his elbows and knees. The lesions were associated with itching and irritation. After using the formulation of Study 4 for two days, the subject's itching stopped. After one week of using the formulation of Study 4, the subject's lesions could no longer be visually detected.

OVERALL CONCLUSIONS

Study 1 demonstrates that the addition of glucosamine to non-prescription strength coal tar cream can make coal tar effective in persons on whom it previously had no effect.

Studies 2 and 3 demonstrate that an emollient cream with anti-inflammatory antioxidants can benefit mild psoriasis but that without the addition of glucosamine, or with a low dose of glucosamine, the effect was limited to that of a super moisturizer with antioxidant activity.

As demonstrated by Study 4, the synergistic interaction of the two herbal extracts with an effective amount of glucosamine yielded an unexpectedly beneficial effect, which could not have been predicted on the basis of the effects of the two herbs alone, or a low concentration of glucosamine with both herbs or with a low concentration of coal tar. It is clear from these studies that an effective amount of glucosamine enhances the therapeutic effect of known therapies like coal tar. Further, glucosamine appears to synergise with agents that alone may have a beneficial effect on mild disease, but which have little effect on moderate to severe disease.

Although the addition of 10% glucosamine to the herbal formulation effected a real improvement in resistant psoriasis, it took a long time to see improvement. However, with 18% glucosamine (even with a lower concentration of the herbal extracts) improvement was rapid and complete within two to three weeks, even for the most resistant lesions. Thus, the use of a relatively high concentration of glucosamine (greater than 10%) was able to boost the anti-inflammatory effects of the berberine and oleuropein, as well as any other healing effects that these herbs may have provided, to effect a non-toxic cure of resistant eczematous lesions, lesions which had not responded (except for very short periods) to UVA, UVB, X-ray, systemic steroids, methotrexate, and many other highly toxic therapies which require close follow-up of the patient to monitor blood cell count, liver toxicity, kidney toxicity, and other serious side effects.

While this invention has been described in reference to illustrative embodiments, this description is not intended to be construed in a limited sense. Various modification and combinations of the illustrative embodiments, as well as other embodiments of the invention, will be apparent to persons skilled in the art upon reference to the description. It is therefore intended that the appended claims encompass any such modifications or embodiments.

What is claimed is:

1. A topical skin preparation adapted-to the treatment of psoriasis, the preparation comprising:
   a pharmaceutically effective amount of glucosamine, or salt thereof, in an approximate amount of more than 5% of the preparation by weight;
   a pharmaceutically effective amount of berberine, or salt thereof, in an approximate amount of at least 1% by weight; and
   a pharmaceutically effective amount of oleuropein, or salts thereof, in an approximate amount of at least 0.5% by weight of the preparation.

2. The preparation of claim 1, further comprising a keratolytic agent.

3. The preparation of claim 2, wherein the keratolytic agent comprises coal tar extract.

4. The preparation of claim 2, wherein the keratolytic agent comprises a salicylate.

5. The preparation of claim 4, wherein the salicylate comprises salicylic acid.

6. The preparation of claim 1, wherein the berberine is from an herbal source.

7. The preparation of claim 1, wherein the oleuropein is from an herbal source.

8. The preparation of claim 1, further comprising an emollient.

9. A topical skin preparation comprising:
   glucosamine, or pharmaceutically acceptable salts thereof, in an approximate amount of more than 5% of the preparation by weight;
   berberine, or pharmaceutically acceptable salts thereof, in an approximate amount of at least 1% by weight; and
   oleuropein, or pharmaceutically acceptable salts thereof, in an approximate amount of at least 0.5% by weight of the preparation.

10. The preparation of claim 9, wherein the preparation is adapted to provide symptomatic relief from psoriasis.

11. The preparation of claim 9, wherein the preparation is adapted to provide symptomatic relief from atopic dermatitis.

12. The preparation of claim 9, wherein glucosamine comprises between about 5–25% of the preparation by weight.

13. The preparation of claim 9, further comprising a keratolytic agent.

14. The preparation of claim 13, wherein the keratolytic agent comprises salicylic acid.

15. The preparation of claim 9, wherein the berberine is a component of a grape seed extract.

16. The preparation of claim 9, wherein the oleuropein is a component of an olive leaf extract.

17. The preparation of claim 9, further comprising an emollient.

18. The preparation of claim 17, wherein the emollient comprises a moisturizing cream.

19. The preparation of claim 9, further comprising a coal tar extract.

20. The preparation of claim 9, wherein glucosamine comprises between about 5–25% by weight, berberine comprises between about 1–10% by weight and oleuropein comprises between about 0.5–7.5% by weight of the preparation.

21. A topical skin preparation comprising glucosamine; berberine and oleuropine, wherein the relative amounts of glucosamine, berberine and oleuropein comprise a ratio of approximately 9:1.75:1 of glucosamine, berberine and oleuropein, respectively.

* * * * *